US00PP28070P3

(12) United States Plant Patent
van Kleinwee

(10) Patent No.: US PP28,070 P3
(45) Date of Patent: May 30, 2017

(54) ***PETUNIA* PLANT NAMED 'PEHY0011'**

(50) Latin Name: *Petunia hybrida*
Varietal Denomination: PEHY0011

(71) Applicant: SYNGENTA PARTICIPATIONS AG, Basel (CH)

(72) Inventor: Theodorus Cornelis van Kleinwee, Enkuizen (NL)

(73) Assignee: Syngenta Participations AG, Basel (CH)

( * ) Notice: Subject to any disclaimer, the term of this patent is extended or adjusted under 35 U.S.C. 154(b) by 13 days.

(21) Appl. No.: 14/757,315

(22) Filed: Dec. 16, 2015

(65) Prior Publication Data

US 2016/0198612 P1 Jul. 7, 2016

Related U.S. Application Data

(60) Provisional application No. 62/099,638, filed on Jan. 5, 2015.

(51) Int. Cl.
*A01H 5/02* (2006.01)

(52) U.S. Cl.
USPC ..... Plt./356.22

(58) Field of Classification Search
USPC ..... Plt./356.1, 356.22
See application file for complete search history.

*Primary Examiner* — Susan McCormick Ewoldt
(74) *Attorney, Agent, or Firm* — Dale Skalla

(57) ABSTRACT

A new *Petunia* plant named 'PEHY0011' particularly distinguished by the relatively large sized, brilliant purple colored flowers, light-green foliage, narrow leaf shape, good branching, and a compact, mounding plant habit.

1 Drawing Sheet

Latin name of the genus and species of the plant claimed: *Petunia hybrida.*

Varietal denomination: 'PEHY0011'.

BACKGROUND OF THE NEW PLANT

The present invention comprises a new *Petunia*, botanically known as *Petunia hybrida*, and hereinafter referred to by the variety name 'PEHY0011'.

'PEHY0011' is a product of a planned breeding program. The new cultivar has fairly large size, red-purple colored flowers with a dark throat, light green foliage, narrow leaf shape, good branching, and compact, mounding plant habit.

'PEHY0011' originated from a hybridization made in October 2010 in a controlled breeding environment in Enkhuizen, Netherlands.

The female parent was the unpatented proprietary plant designated 'N0430-2' with less branching and a darker purple colour than 'PHY0011'.

The male parent of 'PEHY0011' was an unpatented proprietary plant identified as 'P0193' with red flowers and less vigour compared to 'PEHY0011'.

The resulting seeds were sown in February 2011. 'PEHY0011' was selected as a single flowering plant within the progeny of the stated cross May 25, 2011 in a controlled environment in Enkhuizen, Netherlands.

The first act of asexual reproduction of 'PEHY0011' was accomplished when vegetative cuttings were propagated from the initial selection in June 2011 in a controlled environment in Enkhuizen, Netherlands.

BRIEF SUMMARY OF INVENTION

Horticultural examination of plants grown from cuttings of the plant initiated in September 2011 in Angers, France, and continuing thereafter, has demonstrated that the combination of characteristics as herein disclosed for 'PEHY0011' are firmly fixed and are retained through successive generations of asexual reproduction.

'PEHY0011' has not been observed under all possible environmental conditions. The phenotype may vary significantly with variations in environment such as temperature, light intensity, and day length.

A Plant Breeder's Right for this cultivar was applied for in the European Community Plant Variety Office (CPVO) on Jun. 27, 2014, No. 2014/1719. 'PEHY0011' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

Figure 1:
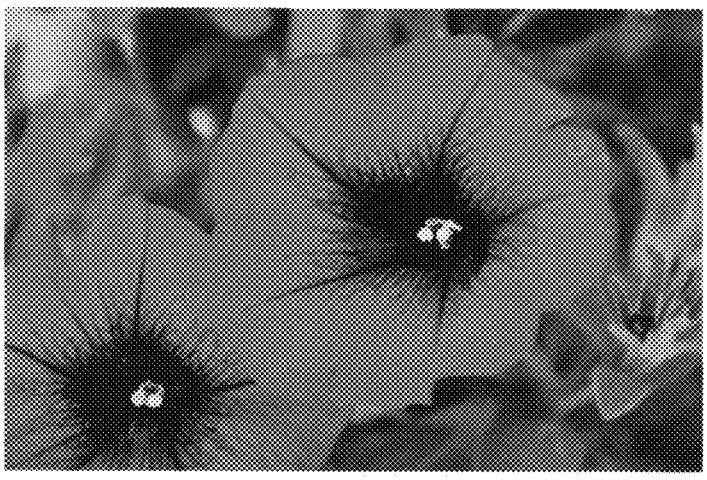
Figure 2:
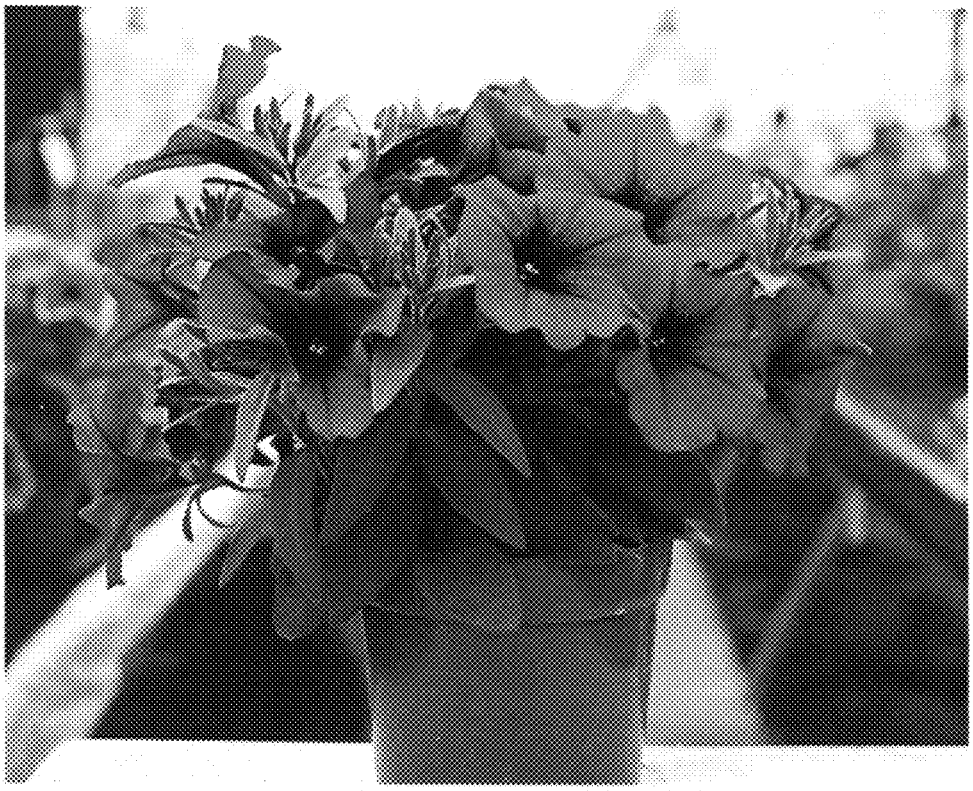

The accompanying photographic drawing shows typical flower and foliage characteristics of 'PEHY0011' with colors being as true as possible with an illustration of this type. The photographic drawing shows in FIG. 1. a close view of a flower, and in FIG. 2 a flowering plant of the new variety.

DETAILED BOTANICAL DESCRIPTION

The plant descriptions and measurements were taken Sep. 29-30, 2014, from plants grown for breeding purposes in a greenhouse in Enkhuizen, Netherlands. The plants had been planted around Jul. 10, 2014. They were 12 weeks old and growing in 19 cm containers. They had been cut back a few weeks before the observations.

The aforementioned photographs were taken in late April 2014 from plants growing in a greenhouse trial in Andijk, Netherlands. These plants were approximately 12-13 weeks of age.

Color references are made to The Royal Horticultural Society Colour Chart (R.H.S.) 2001.

TABLE 1

DIFFERENCES BETWEEN THE NEW VARIETY 'PEHY0011' AND A SIMILAR VARIETY

| | 'PEHY0011' | 'POTUNIA PLUS PURPLE' |
|---|---|---|
| Flower color: | Intermediate between RHS N74A and N78A | Different purple hue, near RHS 71A |
| Leaf shape: | Long, elliptic | Almost circular |

Plant:

*Form, growth and habit*.—Compact and mounding, free flowering.

*Plant height*.—20 cm.

*Plant height* (*inflorescence included*).—23 cm.

*Plant width*.—30 cm.

Roots:

*Number of days to initiate roots*.—About 12 days at about 22 degrees C.

*Number of days to produce a rooted cutting plant*.—18-24 days at about 22 degrees C.

*Type*.—Fine, fibrous, free branching.

*Color*.—RHS N155B.

Foliage:

*Arrangement of leaves*.—Simple, opposite, sometimes decussate.

*Immature leaf, color upper surface*.—RHS 138A, slightly more yellowish.

*Immature leaf, color lower surface*.—RHS 144A.

*Mature leaf, color upper surface*.—RHS 138A, somewhat more yellowish.

*Mature leaf, color lower surface*.—RHS 144A.

*Leaf length*.—8.5-9.5 cm.

*Leaf width*.—Up to 4.3 cm.

*Shape*.—Elliptic.

*Base shape*.—Attenuate.

*Apex shape*.—Obtuse.

*Margin*.—Entire.

*Texture, upper surface*.—Pubescent.

*Texture, lower surface*.—Pubescent, more but shorter hair.

*Color of veins, upper surface*.—RHS 144A.

*Color of veins, lower surface*.—RHS 144B.

*Petiole, color*.—RHS 144C.

*Length*.—0.7 cm.

*Diameter*.—0.5-0.6 cm.

*Texture*.—Pubescent.

Stem:

*Quantity of main branches per plant*.—4.

*Color of stem*.—RHS 143B.

*Length of stem*.—15-20 cm.

*Diameter*.—0.25-0.3 cm.

*Length of internodes*.—3-4 cm.

*Texture*.—Hirsute, glandular hair.

*Color of pedicels*.—RHS 143B, darker on the upper side near the corolla tube and near the internodes: RHS N186C.

*Length*.—2.7-3 cm.

*Diameter*.—0.2 cm.

*Texture*.—Hirsute, glandular hair.

Inflorescence:

*Type of inflorescence*.—Single flowers, emerging from the upper nodes of the stem.

*Blooming habit*.—Continuously through the summer months.

*Start of flowering*.—About 8 weeks from planting rooted cuttings.

*Quantity of flowers per plant*.—About 15-20.

*Lastingness of individual blooms on the plant*.—Up to 2 weeks, depending on temperature.

*Fragrance*.—None.

Bud (just before opening):

*Color*.—RHS N79A to N79B.

*Length*.—4 cm.

*Width*.—1 cm.

*Shape*.—Oblong.

Immature flower:

*Diameter*.—4.5-5 cm.

*Color, upper surface*.—Near RHS N74A or slightly more bluish, very deep color with black veins.

*Color, lower surface*.—RHS 72A to RHS 72B.

Mature flower:

*Shape*.—Salver-shape, with funnel shaped base, formed by 5 fused petals.

*Flower, horizontal diameter*.—6.5 cm.

*Flower, vertical diameter*.—4.5 cm.

*Corolla, color upper surface*.—Intermediate between the tones of RHS N74A and RHS N78A, a less deep hue than with immature flowers; color partly turning to RHS N80A with maturing of the flowers; weak pattern of dark veins, near RHS N186A, on the central part of the 'face'.

*Corolla, color, lower surface*.—RHS 72B.

*Petal apex shape*.—Mucronulate.

*Petal lobation*.—Weak to medium.

*Petal base shape*.—Fused.

*Corolla, margin*.—Entire, somewhat wavy, partly a little reflexed.

*Texture, upper surface*.—Glabrous, papillose.

*Texture, lower surface*.—Papillose, pubescent near the corolla tube.

*Corolla tube, color of inner surface*.—Appears black due the very strong pattern of 'black' veins, RHS N186A; very little background color visible: RHS N74C.

*Corolla tube, color of outer surface*.—RHS 79A.

*Corolla tube, length*.—3 cm.

*Corolla tube, diameter*.—1.4 cm.

*Corolla texture*.—Hirsute outside.

Calyx:

*Form*.—5 sepals in a whorl, fused at the bases.

*Color, upper surface*.—RHS 138A.

*Color, lower surface*.—RHS 143B.

*Sepal, length*.—2.5-3 cm.

*Sepal, width*.—0.3 cm.

*Shape*.—Ensiform.

*Apex shape*.—Acute.

*Base*.—Fused.

*Margins*.—Entire.

*Texture, upper surface*.—Hirsute.

*Texture, lower surface*.—Hirsute with shorter hair than upper surface.

Reproductive organs:

Gynoecium:

*Pistil.*—1.

*Length.*—2.2 cm.

*Style color.*—RHS 145A, RHS N187B near the stigma.

*Style length.*—2 cm.

*Stigma color.*—Upper side is green, RHS 148B, lower side is RHS 87B.

*Stigma shape.*—Flat rounded disc fixed on the style from under.

*Ovary color.*—RHS 143C.

Androecium:

*Stamens.*—5.

*Color of filaments.*—Whiter then RHS 155D.

*Length filaments.*—2 -2.4 cm.

*Anther color.*—RHS 201B.

*Anther length.*—0.15 cm.

*Anther shape.*—Elliptical.

*Color of pollen.*—RHS 188A.

*Pollen amount.*—Plenty.

Fertility/seed set: Has not been observed on this hybrid.

Disease/pest resistance: Has not been observed on this hybrid.

What is claimed is:

1. A new and distinct variety of *Petunia* plant named 'PEHY0011' substantially as illustrated and described herein.

* * * * *